United States Patent [19]
Sawara et al.

[11] Patent Number: 4,906,762
[45] Date of Patent: Mar. 6, 1990

[54] PROCESS FOR PRODUCING TRIALKYLARSENIC COMPOUND

[75] Inventors: Kenichi Sawara; Hidekimi Kadokura; Tadaaki Yako, all of Niihama, Japan

[73] Assignee: Sumitomo Chemical Company, Limited, Osaka, Japan

[21] Appl. No.: 232,671

[22] Filed: Aug. 16, 1988

[30] Foreign Application Priority Data

Aug. 27, 1987 [JP] Japan ................ 62-213948

[51] Int. Cl.$^4$ ................................ C07F 9/72
[52] U.S. Cl. ........................ 556/70; 556/187
[58] Field of Search .................. 556/70, 187

[56] References Cited
U.S. PATENT DOCUMENTS

| | | | |
|---|---|---|---|
| 3,137,716 | 6/1964 | Stamm et al. | 556/70 |
| 3,363,021 | 1/1968 | Tucci | 556/187 |
| 3,519,669 | 7/1970 | Ziegler et al. | 556/187 |
| 3,696,161 | 10/1972 | Kobetz et al. | 556/187 |

*Primary Examiner*—Paul F. Shaver
*Attorney, Agent, or Firm*—Stevens, Davis, Miller & Mosher

[57] ABSTRACT

According to the process of the present invention, trialkylarsenic compounds having a very high purity of usually over 99% can be obtained by using inexpensive, easily available arsenic oxides and without any complicated operations. The trialkylarsenic compounds thus obtained can be effectively used as a material for compound semiconductors in the field of electronic industry as well as in the field of various chemical industries, and are of great industrial value.

12 Claims, No Drawings

PROCESS FOR PRODUCING TRIALKYLARSENIC COMPOUND

The present invention relates to a process for producing trialkylarsenic compounds. More particularly, it relates to a process for producing trialkylarsenic compounds capable of producing intended products of high purity through an easy operation.

As is generally known, alkylarsenic compounds are used as a raw material in chemical and electronic industries. Particularly, thermal decomposition of a mixture of a trialkylarsenic compound with an alkylgallium in gas phase gives gallium arsenide alloy. And the alloy is used in the field of electronic industry as a very useful compound semiconductor.

In such uses, the trialkylarsenic compounds of raw material are required to have as high a purity as possible because the presence of silicon and oxygen impurities in the trialkylarsenic compounds adversely affects the electric properties of the resulting semiconductors.

Various methods have been known for producing trialkylarsenic compounds, which include (1) a method comprising reacting methylmagnesium iodide, one of the Grignard reagents, with arsenic trichloride in n-butyl ether to give trimethylarsenic [for example, Journal of Chemical Society, 3381 (1954)], (2) a method comprising reacting arsenic trichloride in n-hexane with triethylaluminum in n-hexane in the presence of sodium chloride (for example, British Patent No. 820,146), and (3) a method comprising reacting an alkylaluminum with an arsenic oxide or arsenic sulfide (for example, U.S. Pat. No. 3,137,716).

However, the above-mentioned methods have the following disadvantages. In the method (1), an oxygen-containing compound such as an ether is used as the reaction solvent, so that it contaminates the trialkylarsenic compound and lowers the purity thereof when the trialkylarsenic compound is recovered from the reaction mixture by distillation.

In the method (2), arsenic halides are used as a raw material. But they are corrosive to metals, so that corrosion-resistant materials must be used for process equipments. Moreover, arsenic halides are less available than arsenic oxides.

In the method (3), the recovery of trialkylarsenic compounds by distillation is very low presumably because the trialkylarsenic compounds formed react with trialkylaluminum remaining in the reaction system to form complexes. Especially, lower trialkylarsenic compounds markedly show this tendency. Although it is possible to distill the reaction product while heating the same up to a temperature at which the complexes decompose in order to recover the trialkylarsenic compound from the reaction product, such a method is not practical since it requires a high temperature.

Besides the above methods, it is also possible to hydrolyze the alkylaluminum present in the reaction mixture with water to let loose the trialkylarsenic compound and then recover it by distillation. However, this method is economically disadvantageous because it requires an additional step for dehydrating the trialkylarsenic compound recovered by distillation to keep off the adverse effects of contaminating water on the properties of the resulting semiconductor.

In view of the situation, the present inventors have made extensive studies with the aim of developing a process for producing trialkylarsenic compounds comprising using an arsenic oxide which is easily available and non-corrosive to equipment materials, which process is easy to operate and is capable of producing intended products of high purity contaminated with little of water and other impurities. As the result, they have found that adding an alkali metal halide to the mixture of a trialkylarsenic and an alkylaluminum compound suppresses the formation of complexes of the trialkylarsenic with the alkylaluminum compound and that distilling the resulting reaction mixture easily gives trialkylarsenic compound of high purity. The present invention is based on the above findings.

According to the present invention, there is provided a process for producing trialkylarsenic compounds comprising (1) a step of reacting an arsenic oxide with an alkylaluminum compound in an inert gas atmosphere and (2) a step of reacting the reaction mixture obtained through said step (1) with an alkali metal halide.

The trialkylarsenic compounds obtained according to the process of the present invention are those having alkyl groups of 1 to 8 carbon atoms. Specific examples thereof include trimethylarsenic, triethylarsenic, tripropylarsenic, tributylarsenic, tripentylarsenic, trihexylarsenic, triheptylarsenic, trioctylarsenic and the like. Particularly, they are trialkylarsenic compounds wherein the alkyl groups each have 1 to 4 carbon atoms.

As the method for practicing the present invention, mention may be made for example of (A) a method comprising reacting an arsenic oxide with an alkylaluminum compound in an inert gas atmosphere and then adding an alkali metal halide to the reaction system to effect a reaction, and (B) a method comprising mixing an arsenic oxide, an alkylaluminum compound and an alkali metal halide in an inert gas atmosphere, then first reacting the arsenic oxide and the alkylaluminum compound under mild reaction conditions and subsequently reacting the resulting reaction product with the alkali metal halide under more severe reaction conditions.

In the method (A), firstly an arsenic oxide and an alkylaluminum compound are reacted in an atmosphere of such inert gases as nitrogen or argon to obtain a trialkylarsenic compound.

Although this reaction is usually carried out by adding an alkylaluminum compound to a suspended solution of an arsenic oxide dispersed in an inert hydrocarbon solvent, it may also be conducted by adding a suspended solution of an arsenic oxide into an alkylaluminum compound.

The proportion of the alkylaluminum compound used relative to the arsenic oxide is about 3 to about 20 times by mole, preferably about 5 to about 10 times by mole.

The reaction is carried out with stirring at a reaction temperature of about 30° to about 150° C. for a reaction time of about 10 minutes or more, preferably in the range from about 30 minutes to about 3 hours.

Although the reaction temperature is not particularly limited, it is usually about 30° to about 150° C. When the reaction temperature is too low, polymerous by-products formed during the reaction sometimes harden and cause difficulty in stirring the reaction mixture, whereas when the reaction temperature is too high, thermal decomposition of alkylaluminum occurs.

Examples of the inert hydrocarbon solvent used for suspending arsenic oxides are saturated aliphatic hydrocarbons such as hexane, heptane, octane, nonane, decane, undecane, dodecane and paraffin oil; alicyclic hydrocarbons such as cyclohexane and cycloheptane; aromatic hydrocarbons such as benzene, toluene and xylene; and like solvents.

The inert hydrocarbon solvent should be used in such an amount that the arsenic oxide can be uniformly dispersed therein. However, it is usually used in a range of about 1% by volume or more, preferably about 3% to about 30% by volume based on the arsenic oxide.

The arsenic oxides used as a raw material are diarsenic trioxide, diarsenic tetroxide, diarsenic pentoxide or the mixtures thereof, and are not particularly limited. Usually, powdery diarsenic trioxide is used.

The alkylaluminum compounds used in the present invention are alkylaluminum compounds represented by the general formula

wherein $R_1$ denotes an alkyl group having 1 to 8 carbon atoms, and $R_2$ and $R_3$ each independently denote an alkyl group of 1 to 8 carbon atoms or a halogen including chlorine, bromine and iodine.

Specifically, they are trialkylaluminums such as trimethylaluminum, triethylaluminum, tripropylaluminum and tributylaluminum; dialkylaluminum halides such as dimethylaluminum chloride and diethylaluminum chloride; alkylaluminum dihalides such as methylaluminum dichloride and ethylaluminum dichloride; and the mixtures thereof.

After completion of the reaction of an arsenic oxide with an alkylaluminum compound, the resulting reaction solution is mixed with an alkali metal halide to effect a reaction.

Examples of the alkali metal halide used in the present invention are potassium fluoride, sodium fluoride, potassium chloride, sodium chloride, potassium bromide, sodium bromide, potassium iodide, sodium iodide, and the mixtures thereof. Preferably, potassium fluoride, sodium fluoride, potassium chloride, sodium chloride, or the mixture thereof is used.

The amount of the alkali metal halide to be mixed with the reaction solution is about 0.5 to about 12 moles, preferably about 1 to about 5 moles, relative to one mole of the arsenic oxide charged. When the mixed amount is less than the above-mentioned range, the yield of the intended product is low. On the other hand, when the amount is too large, the alkali metal halide, a solid, causes difficulty in stirring.

Mixing the alkali metal halide with the reaction solution may be effected by adding the halide to the solution either at one time or in portions. Of course it may be effected by adding the reaction solution to the alkali metal halide.

The mixed solution of the reaction solution and the alkali metal halide is heat-treated, usually with stirring, at a temperature of about 90° C. to about 200° C., preferably about 100° C. to about 160° C., for about 10 minutes or more, preferably for about 30 minutes to about 3 hours.

In the above heat treatment, when the heating temperature is too low, the yield of intended product is low, whereas when it is too high, the quality of the intended products are damaged by heat.

In general, the higher the heating temperature, the shorter the heating time required.

With regard to the method (A), a detailed description was given above. The process of the present invention can also be carried out by the method (B), which comprises mixing an arsenic oxide, an alkylaluminum compound and an alkali metal halide at the same time. The resulting mixture is heat-treated first in an inert gas atmosphere under the first reaction conditions which allow the reaction of the arsenic oxide with the alkylaluminum compound to form an alkylarsenic compound but do not allow the reaction of the alkali metal halide with the alkylaluminum compound, for example at a temperature of about 30° C. to about 90° C. for 10 minutes or more, preferably at a temperature of about 50° C. to about 85° C. for about 30 minutes to about 3 hours. Subsequently, the resulting mixture is heat-treated under the second reaction conditions which allow the reaction of the alkali metal halide with the alkylaluminum compound, for example at a temperature of about 90° C. or more for 10 minutes or more, preferably at a temperature of about 100° C. to about 160° C. for about 30 minutes to about 3 hours, to effect reactions.

In the above method, the same conditions as in the method (A) described before is adopted relative to the proportion of the added alkylaluminum compound to the arsenic oxide, the proportion of the added alkali metal halide to the arsenic oxide, the raw materials, inert solvents and inert gases to be used, and the methods for distilling and separating the trialkylarsenic compound from the final reaction product.

The reaction solution obtained by the method (A) or (B) is, directly or as occasion demands, after being separated from solid precipitates by decantation, filtration, centrifugation or like means, subjected to a conventional separatory operation.

When distillation is used as the separatory operation, the method of distillation may be appropriately selected depending on the purity of the intended trialkylarsenic compound and other factors. Also, distillation conditions may be determined depending on the properties of the intended trialkylarsenic compound.

The distillation is generally carried out at a pressure of 0.1 to 760 mmHg, preferably about 1 to about 760 mmHg and at a temperature of about 50° C. to about 220° C., preferably about 50° C. to about 160° C.

Needless to say, when the trialkylarsenic compound obtained by distillation is contaminated with a trace amount of solvent, it can be freed from the solvent by redistillation and the like.

According to the process of the present invention described in detail above, trialkylarsenic compounds having a very high purity of usually over 99% can be obtained by using inexpensive, easily available arsenic oxides and without any complicated operations. The trialkylarsenic compounds thus obtained can be effectively used as a material for compound semiconductors in the field of electronic industry as well as in the field of various chemical industries, and is of great industrial value.

The following examples serve to give specific illustrations of the practice of the present invention but they are not intended in any way to limit the scope of the present invention. The yield shown in Examples and Comparative Examples is calculated based on the amount of diarsenic trioxide charged.

EXAMPLE 1

A reaction apparatus comprising a glass flask of 1 liter inner volume equipped with a stirrer and a reflux condenser was used. Air in the flask and condenser was replaced with nitrogen and then 70 g of diarsenic trioxide and 400 ml of n-dodecane were introduced in the flask.

The flask was heated to 60° C. and then, with stirring, 180 g of trimethylaluminum were gradually added from a dropping funnel by drops. Thereafter the resulting mixed solution was heated with stirring at 80° C. for 2 hours. Then, the reaction solution was cooled down to room temperature, then 75 g of potassium fluoride were added thereto, and the mixture was heat-treated at 130° C. for 1 hour.

The reaction solution thus obtained was subjected to simple distillation at normal pressure and then to rectification to obtain 25 g (60% yield) of trimethylarsenic having a purity of 99.99%.

EXAMPLE 2

Into the same apparatus as in Example 1 were introduced 60 g of diarsenic trioxide, 300 ml of n-dodecane and 53 g of potassium fluoride. Then, 207 g of triethylaluminum were gradually added thereto.

The resulting mixture was heated with stirring at 80° C. for 2 hours and then at 140° C. for 2 hours. The reaction solution thus obtained was subjected to simple distillation at a pressure of 100 mmHg and then to rectification to obtain 32 g (65% yield) of triethylarsenic having a purity of 99.99%.

EXAMPLE 3

Into the same apparatus as in Example 1, were introduced 60 g of diarsenic trioxide and 300 ml of n-dodecane, then the resulting mixture was heated to 50° C., and 253 g of diethylaluminum chloride were gradually added thereto in the same manner as in Example 1.

The reaction mixture was heated with stirring at 90° C. for 2 hours and cooled down to room temperature. Then 45 g of potassium chloride were added thereto, and the mixture was heated with stirring at 140° C. for 2 hours.

The reaction solution thus obtained was subjected to simple distillation at a pressure of 100 mmHg and then to rectification to obtain 21 g (43% yield) of triethylarsenic having a purity of 99.9%.

Comparative Example 1

Into the same apparatus as in Example 1 were introduced 70 g of diarsenic trioxide and 400 ml of n-dodecane, the resulting mixture was heated to 60° C., and then 180 g of trimethylaluminum were gradually added thereto.

The reaction mixture was heated with stirring at 80° C. for 2 hours and then at 130° C. for 1 hour.

The reaction solution thus obtained was subjected to simple distillation at normal pressure to obtain 2 g (5% yield) of trimethylarsenic.

What is claimed is:

1. A process for producing a trialkylarsenic compound comprising (1) a step of reacting an arsenic oxide with an alkylaluminum compound in an inert gas atmosphere and (2) a step of reacting the reaction mixture obtained through the step (1) with an alkali metal halide.

2. A process according to claim 1, wherein the reaction of step (1) is carried out at about 30° C. to 150° C. for 10 minutes or more, then an alkali metal halide is added to the reaction system and the resulting mixture is allowed to react at 90° C. to 200° C. for 10 minutes or more.

3. A process according to claim 2, wherein the reaction time of each of steps (1) and (2) is 30 minutes to 3 hours and the reaction temperature of step (2) is 100° C. to 160° C.

4. A process according to claim 1, wherein an arsenic oxide, an alkylaluminum compound and an alkali metal halide are mixed in an inert gas atmosphere, then the step (1) is carried out at a temperature of from about 30° C. to less than 90° C. for 10 minutes or more and subsequently the step (2) is carried out at a temperature of 90° C. or more for 10 minutes or more.

5. A process according to claim 4, wherein the reaction temperature of step (1) is 50° C. to 85° C. and the reaction time is 30 minutes to 3 hours, and the reaction temperature of step (2) is 100° C. to 160° C. and the reaction time is 30 minutes to 3 hours.

6. A process according to claim 1, which further involves a step (3) of separating and recovering the trialkylarsenic compound from the mixed solution of reaction products obtained through the steps (1) and (2).

7. A process according to claim 1, wherein the means of separation and recovery is distillation.

8. A process according to claim 1, wherein the arsenic oxide is diarsenic trioxide.

9. A process according to claim 1, wherein the alkyl groups of the alkylaluminum compound each have 1 to 8 carbon atoms.

10. A process according to claim 1, wherein the amount of the alkylaluminum compound added is 3 to 20 moles relative to one mole of the arsenic oxide.

11. A process according to claim 1, wherein the alkali metal halide is at least one member selected from the group consisting of potassium fluoride, sodium fluoride, potassium chloride and sodium chloride.

12. A process according to claim 1, wherein the amount of the alkali metal halide added is 0.5 to 12 moles relative to one mole of the arsenic oxide.

* * * * *